US00PP36832P2

(12) United States Plant Patent
Lim

(10) Patent No.: US PP36,832 P2
(45) Date of Patent: Jul. 15, 2025

(54) ***AGAPANTHUS* PLANT NAMED 'ALTatomicage'**

(50) Latin Name: *Agapanthus hybrid*
Varietal Denomination: ALTatomicage

(71) Applicant: Altman Specialty Plants llc, Vista, CA (US)

(72) Inventor: Peter Lim, Escondido, CA (US)

(73) Assignee: Altman Specialty Plants llc, Vista, CA (US)

( * ) Notice: Subject to any disclaimer, the term of this patent is extended or adjusted under 35 U.S.C. 154(b) by 0 days.

(21) Appl. No.: 19/022,422

(22) Filed: Jan. 15, 2025

(51) Int. Cl.
*A01H 5/02* (2018.01)
*A01H 6/04* (2018.01)

(52) U.S. Cl.
USPC ..... Plt./398

(58) Field of Classification Search
USPC ..... Plt./398
See application file for complete search history.

*Primary Examiner* — Susan McCormick Ewoldt
*Assistant Examiner* — Zachariah Allan Kay
(74) *Attorney, Agent, or Firm* — Cassandra Bright

(57) ABSTRACT

A new and distinct cultivar of *Agapanthus* plant named 'ALTatomicage' is disclosed, characterized by a dwarf growth habit, reaching about 25 cm high. Inflorescences are medium-sized and composed of medium blue flowers Flowering stems (scapes) are thick. The new variety is an *Agapanthus*, typically produced as an ornamental plant.

1 Drawing Sheet

Latin name of the genus and species: *Agapanthus* hybrid.
Variety denomination: 'ALTatomicage'.

BACKGROUND OF THE INVENTION

The new *Agapanthus* cultivar is the product of a planned breeding program conducted by the inventor, Peter Lim. The cross resulting in this new variety was made in August of 2018 at a commercial nursery in Vista, California.

The seed parent is the *Agapanthus* 'ALTbloom' U.S. Plant Pat. No. 33,968. The pollen parent is an unnamed, unpatented proprietary *Agapanthus*. The new variety was identified and selected as a potentially interesting selection in October of 2020, at a commercial nursery in Vista, California.

Asexual reproduction of the new cultivar 'ALTatomicage' was first performed in Oct. 10, 2020, in Vista, California, by vegetative rhizome division. Subsequent propagation has shown that the unique features of this cultivar are stable and reproduced true to type in successive generations.

SUMMARY OF THE INVENTION

The cultivar 'ALTatomicage' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ALTatomicage'. These characteristics in combination distinguish 'ALTatomicage' as a new and distinct *Agapanthus* cultivar:

1. Dwarf size, reaching about 25 cm.
2. Thick flowering stem.
3. Medium sized flowers
4. Blue flowers.

PARENT COMPARISON

Plants of the new cultivar 'ALTatomicage' are similar to plants of the seed parent, in most horticultural characteristics. However, characteristics of the new cultivar differ in the following:

1. The new variety is shorter than the seed parent.
2. The new variety has medium blue flowers; the seed parent has light blue flowers.

Plants of the new cultivar 'ALTatomicage' are similar to plants of the pollen parent, in most horticultural characteristics. However, the new cultivar differs in the following:

1. The new variety is shorter than the pollen parent.
2. The new variety has medium blue flowers; the pollen parent has dark blue flowers.

COMMERCIAL COMPARISON

Plants of 'ALTatomicage' are similar in some horticultural characteristics to the variety *Agapanthus* 'Benfran', U.S. Plant Pat. No. 21,705. The new variety, however, differs in the following:

1. 'ALTatomicage' has medium blue flowers; 'Benfran' has lightly blue flowers.
2. 'ALTatomicage' begins flowering earlier than 'Benfran'.

Plants of 'ALTatomicage' are similar in some horticultural characteristics to the variety *Agapanthus* 'AMBIC001', U.S. Plant Pat. No. 25,519. The new variety, however, differs in the following:

1. 'ALTatomicage' has thicker flower stems than 'AMBIC001'.
2. 'ALTatomicage' has smaller inflorescences than 'AMBIC001'.
3. 'ALTatomicage' has blue flower buds; 'AMBIC001' has creamy white flower buds that open bicolored.

BRIEF DESCRIPTION OF THE PHOTOGRAPH

The accompanying photograph illustrates in full color typical plants of 'ALTatomicage' grown in a commercial hoop-house in Vista, California. The plants are approximately one year old, grown one-gallon pots. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe an 'ALTatomicage' plant. This plant was grown outdoors in a 2-gallon pot, in Camarillo, California. Plants are approximately 1 year old. Temperatures ranged from 15° C. to 40° C. during the day, and from 10° C. to 25° C. at night. No artificial light, photoperiodic treatments were given to the plants. Measurements and numerical values represent averages of typical plant types.

Botanical classification: *Agapanthus* hybrid 'ALTatomicage'.

PROPAGATION

Propagation method: Rhizome division.

Root description: Long single root with limited branching.

PLANT

Age of plant described: 240 days from a rooted cutting.

Growth habit: Clump forming tender perennial with arching, pendulous foliage. Plants evergreen to about −5° C.

Height: Foliar plane 15 cm. Flowering plane 25 cm.

Plant spread: Approximately 15 to 25 cm.

Growth rate: Moderate.

FOLIAGE

Leaf:

- *Arrangement*.—Basal whorls.
- *Quantity*.—Average 12 to 18 per clump.
- *Average length*.—10 to 15 cm.
- *Average width*.—1.5 cm.
- *Shape of blade*.—Linear.
- *Apex*.—Acute.
- *Base*.—Truncate, non-clasping.
- *Margin*.—Entire.
- *Aspect*.—Very slightly recurved.
- *Texture of top surface*.—Glabrous.
- *Texture of bottom surface*.—Glabrous.
- *Color*.—Young foliage upper side: Near RHS Green 143B. Young foliage under side: Near RHS Green 143B. Mature foliage upper side: Near RHS Green 137C. Mature foliage under side: Near RHS Green 137C.

FLOWER

Natural flowering season: Begins flowering between May and early June in Southern California.

Length of flowering period: Approximately 8 weeks.

Inflorescence type: Terminal Umbel with approximately 20 to 25 individual flowers and 6 to 8 buds.

Individual flower type: Single.

Flower profile: Funnelform.

Lasting quality: Inflorescence shows no significant signs of aging for approximately 5 to 6 weeks.

Bud: Measured at approximately 2 to 5 days from opening.

- *Shape*.—Narrow ovate.
- *Length*.—Approximately 2.5 cm.
- *Diameter*.—Approximately 7 mm.
- *Color*.—Near RHS Violet-Blue 93A.

Umbel size:

- *Diameter*.—Average 8 cm.
- *Height*.—Average 6 cm.

Corolla:

- *Arrangement*.—Apetalous, single, campanulate flowers composed of 6 basally fused tepals, shaped into a flared trumpet.
- *Length*.—Approximately 2.8 cm.
- *Width*.—Approximately 2.4 cm at widest point.
- *Lobe length*.—Approximately 1.5 cm.
- *Lobe width*.—Average 5 mm.
- *Margin*.—Entire.
- *Shape*.—Lanceolate.
- *Apex*.—Broadly acute or obtuse.
- *Texture*.—Glabrous all surfaces.

Color:

- *Tepals*.—When opening, upper surface: Near RHS Violet-Blue 96A. When opening, lower surface: Near RHS Violet-Blue 96A. Fully opened, upper surface: Near RHS Violet-Blue 96B. Fully opened, lower surface: Near RHS Violet-Blue 96C.

Sepals: Not present.

Perianth tube:

- *Length*.—1.2 cm.
- *Width*.—4 mm.
- *Color*.—Inner surface: Near RHS Violet-Blue 96D. Outer surface: Near RHS Violet-Blue 96C.

Fragrance: Faint musty scent.

REPRODUCTIVE ORGANS

Stamens:

- *Protrusion*.—Weak protrusion past the floral lobe apex.
- *Filament color*.—Upper section near RHS Violet-Blue 96A; lower section near 97A.

Anthers:

- *Quantity*.—6.
- *Length*.—Approximately 3 mm.
- *Color*.—Near RHS Violet-Blue 96A.

Pistil:

- *Number*.—1.
- *Length*.—Approximately 2 cm.
- *Style*.—Color: Near RHS Violet-Blue 96D.
- *Stigma*.—Shape: Linear. Color: Near RHS Violet-Blue 96A.

Scape:

- *Length*.—Average 20 cm.
- *Width*.—7 to 10 mm.
- *Texture*.—Glabrous.
- *Color*.—Near RHS Green 143C.

Pedicel:

- *Length*.—1 to 1.5 cm.
- *Width*.—2 mm.

*Texture*.—Glabrous.

*Color*.—Near RHS Green 143C.

Fragrance: None.

OTHER CHARACTERISTICS

Seeds: Not observed to produce seeds.

Disease/pest resistance: Neither resistance no susceptibility to normal diseases and pests of *Agapanthus*.

Temperature tolerance: Not tested but expected to tolerate −5° C. to about 40° C.

Drought tolerance: Will tolerate considerable dryness once established.

What is claimed is:

1. A new and distinct cultivar of *Agapanthus* plant named 'ALTatomicage' as herein illustrated and described.

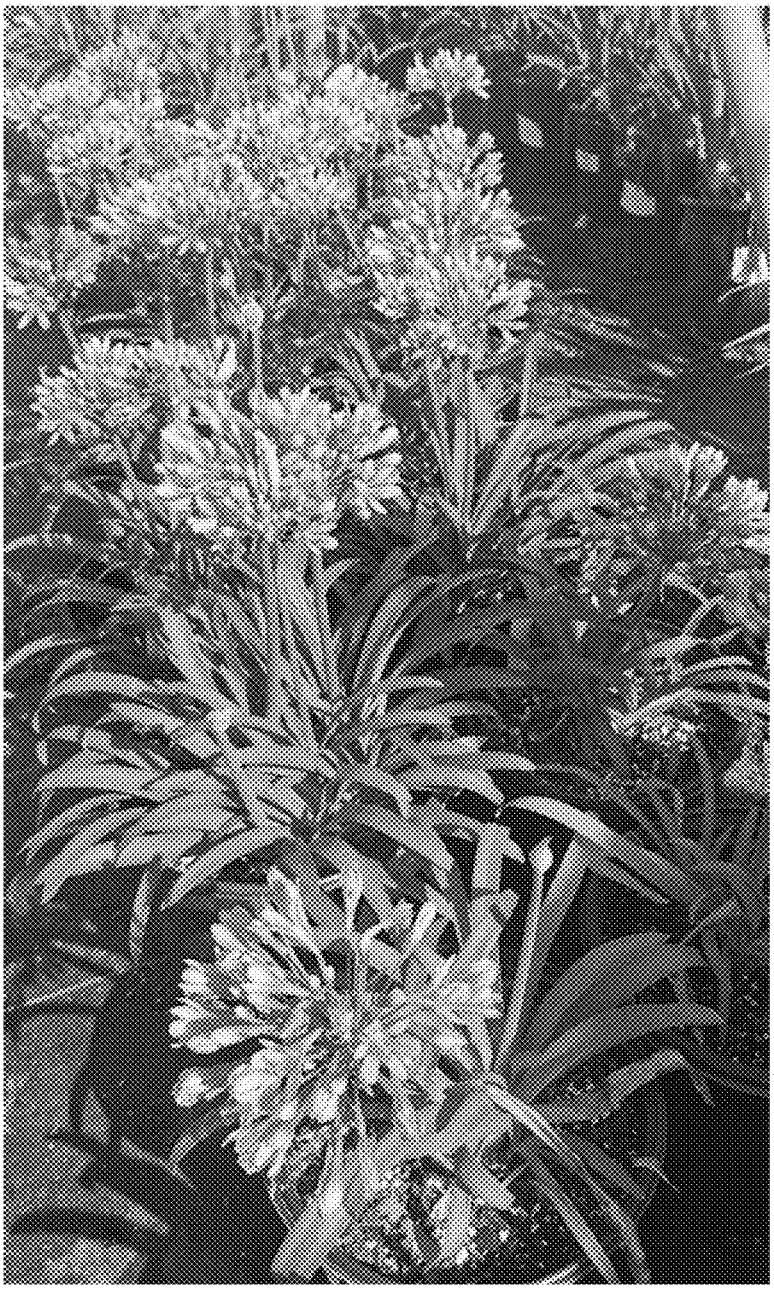

* * * * *